(12) United States Patent
Moore et al.

(10) Patent No.: US 7,414,252 B2
(45) Date of Patent: Aug. 19, 2008

(54) METHOD AND APPARATUS FOR THE AUTOMATED PROCESS OF IN-SITU LIFT-OUT

(75) Inventors: Thomas M. Moore, Dallas, TX (US); Lyudmila Zaykova-Feldman, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 459 days.

(21) Appl. No.: 11/265,934

(22) Filed: Nov. 3, 2005

(65) Prior Publication Data

US 2006/0091325 A1  May 4, 2006

Related U.S. Application Data

(60) Provisional application No. 60/624,650, filed on Nov. 3, 2004.

(51) Int. Cl.
G21G 5/00 (2006.01)

(52) U.S. Cl. ............... 250/492.21; 250/307; 250/492.3; 250/311

(58) Field of Classification Search ........................ None
See application file for complete search history.

(56) References Cited

U.S. PATENT DOCUMENTS

| | | | |
|---|---|---|---|
| 5,270,552 A | 12/1993 | Ohnishi et al. | |
| 5,805,448 A | 9/1998 | Lindsay et al. | |
| 5,986,264 A * | 11/1999 | Grunewald | 250/310 |
| 6,080,991 A | 6/2000 | Tsai | |
| 6,300,631 B1 | 10/2001 | Shofner | |
| 6,417,512 B1 * | 7/2002 | Suzuki | 250/307 |
| 6,522,776 B1 | 2/2003 | Ehrichs | |
| 6,524,873 B1 | 2/2003 | Satya et al. | |
| 6,527,967 B1 | 3/2003 | Suzuki | |
| 6,538,254 B1 * | 3/2003 | Tomimatsu et al. | 250/442.11 |
| 6,566,885 B1 | 5/2003 | Pinto et al. | |
| 6,576,910 B2 | 6/2003 | Hashikawa et al. | |
| 6,608,307 B1 | 8/2003 | Baur | |
| 6,664,552 B2 * | 12/2003 | Shichi et al. | 250/492.21 |
| 6,714,289 B2 | 3/2004 | Haraguchi | |
| 6,717,156 B2 * | 4/2004 | Sugaya et al. | 250/440.11 |
| 6,744,268 B2 | 6/2004 | Hollman | |
| 6,777,656 B2 | 8/2004 | Narita et al. | |
| 6,794,663 B2 * | 9/2004 | Shichi et al. | 250/492.21 |
| 6,795,599 B2 | 9/2004 | Spirin et al. | |
| 6,828,566 B2 * | 12/2004 | Tomimatsu et al. | 250/442.11 |

(Continued)

OTHER PUBLICATIONS

Altmann, F., FIB-Pinpointed Preparation of TEM Samples by a Needle Based Manupulator (Lift-Out) Technique, Practical Metallography, 2003, pp. 175-183, vol. 40, No. 4.

(Continued)

*Primary Examiner*—David A. Vanore
(74) *Attorney, Agent, or Firm*—John A. Thomas

(57) ABSTRACT

An apparatus for performing automated in-situ lift-out of a sample from a specimen includes a computer having a memory with computer-readable instructions, a stage for a specimen and a nano-manipulator. The stage and the nano-manipulator are controlled by motion controllers connected to the computer. The nano-manipulator has a probe tip for attachment to samples excised from the specimen. The computer-readable instructions include instructions to cause the stage motion controllers and the nano-manipulator motion controllers, as well as an ion-beam source, to automatically perform in-situ lift-out of a sample from the specimen.

65 Claims, 3 Drawing Sheets

U.S. PATENT DOCUMENTS

| | | | |
|---|---|---|---|
| 6,841,788 B1 * | 1/2005 | Robinson et al. | 250/492.3 |
| 6,867,606 B2 | 3/2005 | Pinto et al. | |
| 6,889,113 B2 | 5/2005 | Tasker et al. | |
| 6,927,391 B2 | 8/2005 | Tokuda et al. | |
| 6,960,765 B2 * | 11/2005 | Tomimatsu et al. | 250/310 |
| 6,963,068 B2 * | 11/2005 | Asselbergs et al. | 250/311 |
| 6,982,429 B2 * | 1/2006 | Robinson et al. | 250/492.3 |
| 7,002,150 B2 * | 2/2006 | Iwasaki et al. | 250/307 |
| 7,095,024 B2 * | 8/2006 | Adachi et al. | 250/311 |
| 7,268,356 B2 * | 9/2007 | Shichi et al. | 250/492.21 |
| 7,301,146 B2 * | 11/2007 | Tomimatsu et al. | 250/310 |
| 7,326,942 B2 * | 2/2008 | Shichi et al. | 250/492.21 |
| 2002/0000522 A1 | 1/2002 | Alani | |
| 2002/0050565 A1 | 5/2002 | Tokuda et al. | |
| 2002/0195576 A1 | 12/2002 | Inoue et al. | |
| 2003/0150836 A1 | 8/2003 | Tsung et al. | |
| 2003/0236586 A1 | 12/2003 | Tomimatsu et al. | |
| 2004/0004186 A1 | 1/2004 | Jiyan et al. | |
| 2004/0016880 A1 | 1/2004 | Reiner et al. | |
| 2004/0061872 A1 | 4/2004 | Nakano | |
| 2004/0102934 A1 | 5/2004 | Chang | |
| 2004/0125079 A1 | 7/2004 | Kaneko et al. | |
| 2004/0129867 A1 | 7/2004 | Mackey | |
| 2004/0129868 A1 | 7/2004 | Kilmartin | |
| 2004/0129897 A1 | 7/2004 | Adachi et al. | |
| 2004/0144924 A1 | 7/2004 | Asselbergs et al. | |
| 2004/0151417 A1 | 8/2004 | Lagakos et al. | |
| 2004/0188611 A1 | 9/2004 | Takeuchi et al. | |
| 2004/0251412 A1 | 12/2004 | Tappel | |
| 2004/0251413 A1 | 12/2004 | Suzuki et al. | |
| 2005/0001164 A1 | 1/2005 | Tokuda et al. | |
| 2005/0035302 A1 | 2/2005 | Morrison | |
| 2005/0054115 A1 | 3/2005 | Von Harrach et al. | |
| 2005/0184028 A1 | 8/2005 | Baur et al. | |
| 2005/0184236 A1 | 8/2005 | Baur et al. | |
| 2005/0188309 A1 | 8/2005 | Tasker et al. | |

OTHER PUBLICATIONS

Anderson, R., Comparison of FIB TEM Specimen Preparation Methods, Microscopy and Microanalysis, 2002, p. 44, vol. 8, Suppl. 2.

Burkhardt, C., Nisch, W., In-Situ Lift-Out of TEM—Samples by Micro Manipulation in a Scanning Electron Microscope, Practical Metallography, 2004, pp. 190-198, vol. 41.

Kempshall, B. W.; Schwarz, S. M.; Giannuzzi, L. A., In-situ FIB Lift-ouot for site specific TEM specimen preparation of grain boundaries and interfaces, ICEM 15, 2002, pp. 249.

Kempshall, B. W. and Giannuzzi, L. A., In-Situ Lift-Out Specimen Preparation of TEM of Magnetic Materials, Microscopy and Microanalysis, 2002, pp. 390-391, vol. 8, Supp.

Langford, R. M., Petford-Long, A. K. and Gnauck, P., Focused Ion Beam Based Sample Preparation Techniques, Microscopy & Microanalysis, 2002, pp. 46-47, vol. 8, Suppl. 2, Lee.

Chuang, J. H., A Novel Application of the FIB Lift-out Technique for 3-D TEM Analysis, Microeleectronics Reliability, 2001, pp. 1551-1556, vol. 41.

Ritz, Y., Stegmann, H., Engelmann, H. J., Zschech, E., Target Preparation of Samples for 3-D TEM Using Micromanipulator, Practical Metallography, 2004, pp. 180-189, vol. 41.

Veirman De, A.E.M., '3-Dimensional' TEM silicon-device analysis by combining plan-view and FIB sample preparation, Materials Science & Engineering B, 2003, pp. 63-69.

N. Bicais-Lepinay, et al, Lift-out techniques coupled with advanced TEM characterization methods for electrical failure analysis, Microelectronics Reliability 42 (2002) 1747-1742.

E.J. Crawford, focused Ion Beam Sectioning and Lift-out Method for Copper and Resist Vias in Organic Low-k Dielectrics, Microscopy Society of Ameria 2002, pp. 502-506.

J.Y. Dai, Development of a rapid and automated TEM sample preparation method in semiconductor failure analysis and the study of the relevant TEM artifact, Microelectronics Journal 32 (2001) 221-226.

Hans-Jurgen Engelmann, From SEM Cross-Section to TEM Sample - New Capabilites of FIB Sample Preparation by "Refill" Technique, Jul. 24, 2002.

P. Gnauck, Enhanced Site specific Preparation of SEM Cross Sections and TEM Samples by using CrossBeam Technology, Microsc. Microanal. 8 (Suppl. 2), 2002, Microscopy Society of America 2002, pp. 546-547.

T. L. Shofner, et al, Planar TEM Analysis of Nanoindented Samples Using the Focused ION Beam Lift-out Technique, 26th International Symposium for Testing and Failure Analysis, Nov. 12-16 , 2000, Bellevue, Washington, pp. 459-461.

F. A. Stevie, et al, Plain View TEM Sample Preparation Using The Focused Ion Beam Lift-Out Technique, CP449, Characterization and Metrology for ULSI Technology: 1998 The American Institute of Physics, pp. 868-872.

Raghaw Rai, et al, Specific Area Planar and Cross-Sectional Lift-Out Techniques: Procedures and Novel Applications, Proceeding from the 26th International Symposium for Testing and Failure Analysis, Nov. 12-16, 2002, Bellevue, Washington, pp. 415-421.

K. N. Mohammad, Novel Application of FIB Lift-Out and Ultramicrotomy For Advanced Package Failure Analysis,, Proceedings of 9th IPFA 2002, Singapore, pp. 159-163.

P. Gnauck, et al, Real Time SEM Imaging of FIB Miling Processes for Extended Accuracy onTEM Samples for EFTEM Analysis, Proceedings from the 29th International Symposium for Testing and Failure Analysis, Nov. 2-6 2003, Santa Clara, CA, pp. 132-139.

International Searching Authority, International Application No. PCT/US05/39942, International Search Report and the Written Opinion, May 6, 2008.

International Preliminary Examining Authority, International Application No. PCT/US05/39942, International Preliminary Report on Patentability, Jun. 23, 2008.

* cited by examiner

METHOD AND APPARATUS FOR THE AUTOMATED PROCESS OF IN-SITU LIFT-OUT

CLAIM FOR PRIORITY

This application claims the priority of U.S. provisional application Ser. No. 60/624,650, filed Nov. 3, 2004.

CROSS-REFERENCE TO RELATED APPLICATIONS

The present application is related to:

U.S. patent application Ser. No. 10/896,596, filed Jul. 22, 2004, and having the title of: "Method and apparatus for rapid sample preparation in a focused ion beam microscope;"

U.S. patent application Ser. No. 11/186,072, filed Jul. 21, 2005, and having the title of: "Strain detection for automated nano-manipulation;" and, U.S. patent application Ser. No. 11/186,073, filed Jul. 21, 2005, and having the title of: "Method and apparatus for in-situ probe tip replacement inside a charged particle beam microscope."

TECHNICAL FIELD

This application relates to automated processes for the lift-out and preparation of samples inside instruments such as focused ion-beam microscopes.

BACKGROUND

The use of focused ion-beam (FIB) microscopes has become common for the preparation of specimens for later analysis in the transmission electron microscope (TEM). The structural artifacts, and even some structural layers, in the device region and interconnect stack of current integrated-circuit devices can be too small to be reliably detected with the secondary electron imaging in a Scanning Electron Microscope (SEM), or FIB, which offers a bulk surface imaging resolution of approximately 3 nm. In comparison, TEM inspection offers much finer image resolution (<0.1 nm), but requires electron-transparent (<300 nm thick) sections of the sample mounted on 3 mm diameter grid disks.

The in-situ lift-out technique is a series of FIB milling and sample-translation steps used to produce a site-specific specimen for later observation in a TEM or other analytical instrument. During in-situ lift-out, a wedge-shaped section (the "lift-out sample") of material containing the region of interest is first completely excised from the bulk sample, such as a semiconductor wafer or die, using ion-beam milling in the FIB. This lift-out sample is typically 10×5×5 μm in size. Removal of the lift-out sample is then typically performed using an internal nano-manipulator in conjunction with the ion-beam assisted chemical-vapor deposition (CVD) process available with the FIB tool.

The process of in-situ lift-out is a procedure of several successive steps, where the starting point is the delivery of a wafer, having the area of interest, and the probe tip inside the FIB vacuum chamber, and the end point is the lift-out sample ready for the TEM investigation. There is a need in the industry to have the entire process automated, thus allowing for fast and safe processing of a lift-out sample without the need to vent the vacuum chamber or to remove the probe and sample through an airlock.

The reader should note, however that the field of application is limited neither to automated lift-out systems, nor to semiconductor samples. Other objects of interest could be micro-mechanical systems, or biological specimens. Further, in-situ lift-out can be carried out in an atmosphere instead of a vacuum, when the nature of the specimen permits.

DRAWINGS

DESCRIPTION

The preferred embodiment includes a novel method and apparatus for the fully automated process of in-situ lift-out inside a FIB vacuum chamber using an in-situ probe tip replacement system. Although as stated, the field of application is limited neither to automated lift-out systems, nor to semiconductor samples.

Figure 1:
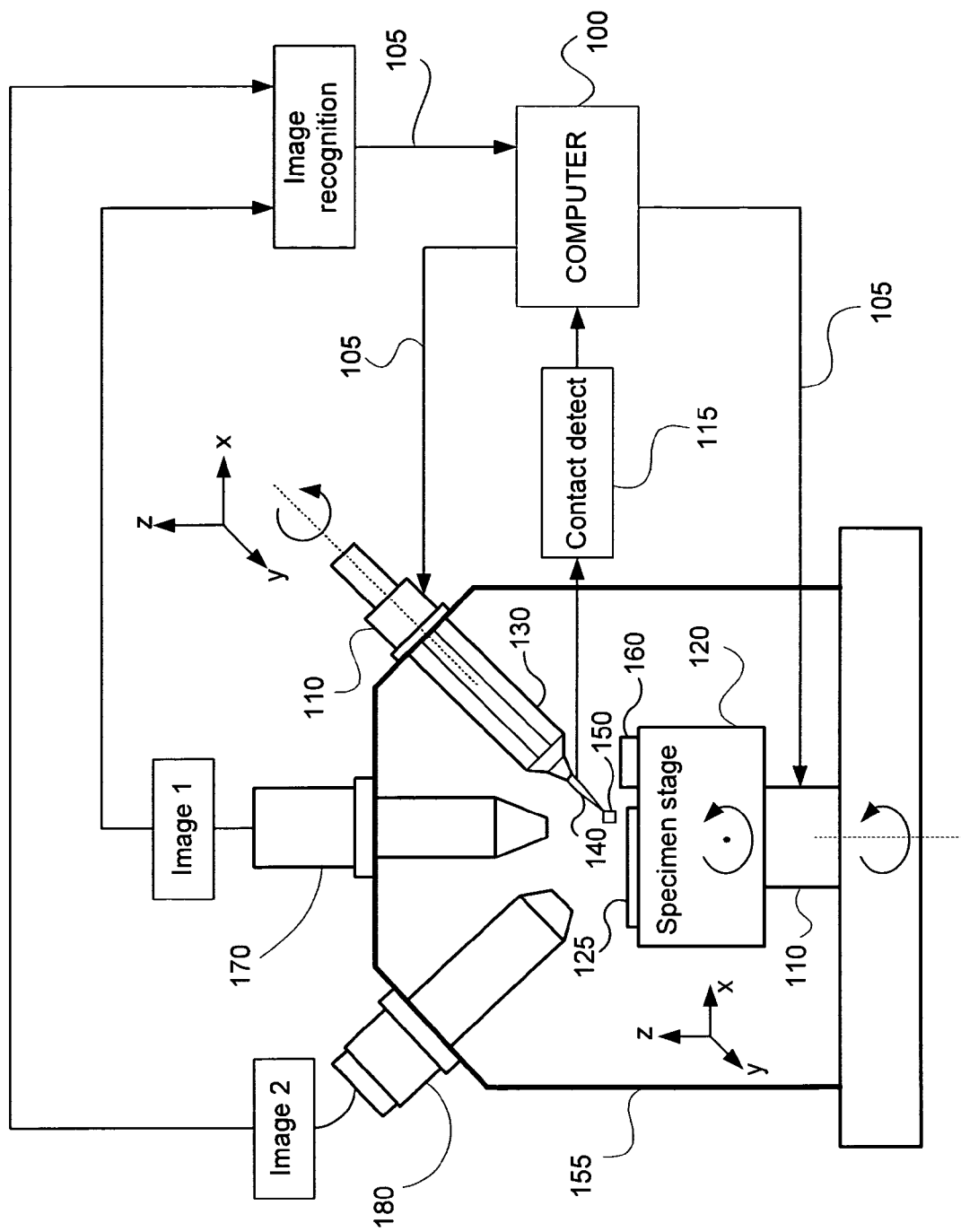
FIG. 1 is a block diagram of an apparatus for carrying out the method of the preferred embodiment.

FIG. 1 shows schematically the automation system to control the process, comprising a computer (100) running a set of computer-readable instructions, and a set of hardware items for the in-situ probe tip replacement system. Such hardware is typically a nano-manipulator (130), probe tips (140), cassettes (160) for holding probe tips (140). The size of the lift-out sample (150) in FIG. 1 is exaggerated for clarity. A suitable nano-manipulator system is the Omniprobe Auto-Probe™ 200 manufactured by Omniprobe, Inc., of Dallas, Tex. Also shown in FIG. 1 are the electron-beam source (170) and ion-beam source (180) that are typical components of a FIB. In the preferred embodiment, the electron beam (170) and the ion-beam sources are operatively connected to the computer (100) so that their imaging and (in the case of the ion-beam) their milling and deposition functions are controlled by the instructions in the computer (100), to assist the lift-out process.

FIG. 1 shows that the computer (100) is operatively connected by suitable circuitry (105) to conventional motion controllers (110) inside and outside the FIB chamber (155), thus allowing movement of the specimen stage (120) and the nano-manipulator (130) probe tip (140) in all necessary degrees of freedom. The computer (100) is preferably a general-purpose programmable computer accepting programs stored on computer-readable media, although special-purpose computers having a CPU, memory, and one or more mass storage devices could be built and used. For example, a suitable computer system (100) is a model Dimension XPS 600, by Dell Computers of Austin, Tex., having a National Instruments NI PCI-7354 4-Axis Stepper/Servo Motion Controller for PCI, as well as a keyboard and display (not shown). The computer (100) is preferably connected to the FIB and nano-manipulator hardware by high-speed parallel communication cables, although, depending on the hardware chosen, the circuitry (105) could include serial data transmission. The box in FIG. 1 labeled "Image recognition" represents processes executing in the computer (100) to compute the location of the probe tip (140) from images of it from the differently oriented electron-beam source (170) and ion-beam source (180).

The disclosed processes can be implemented in a high-level programming language, such as C++.

FIG. 1 also depicts a specimen (125) (usually a wafer) on the specimen stage (120), and the means for detecting contact (115) of the probe tip (140) with a surface (discussed below).

In the following description, well-known parts or processes have been shown in block diagram form in order not to obscure the present disclosure in unnecessary detail. For the most part, details concerning timing considerations and the like have been omitted in as much as such details are not necessary to obtain a complete understanding of the present disclosure and are within the skills of persons of ordinary skill in the relevant art.

The setup process (200) includes all necessary steps to identify the target position on the specimen (125) at the eucentric position in the microscope, as well as mechanical alignment, initialization of the mechanical automation system, and loading of probe tips (140) and the probe-tip exchange cassette (160).

While setting up the system, several approaches can be used. One would be the one-probe tip approach, where a single probe tip (140) is loaded ahead of time in the probe shaft of a nano-manipulator (130) and used for a single lift-out operation. In another approach, a set of probe tips (140) is used. These probe tips (140) fill in the whole length of a hollow probe shaft (not shown), and the extra number of probe tips (140) is loaded ahead of time into an interchangeable magazine (not shown), located outside the FIB, so the supply of the probe tips (140) can be continuous and uninterrupted. Such a system of multiple probe tips is described in co-pending application Ser. No. 11/186,073, cited above.

Figure 2:
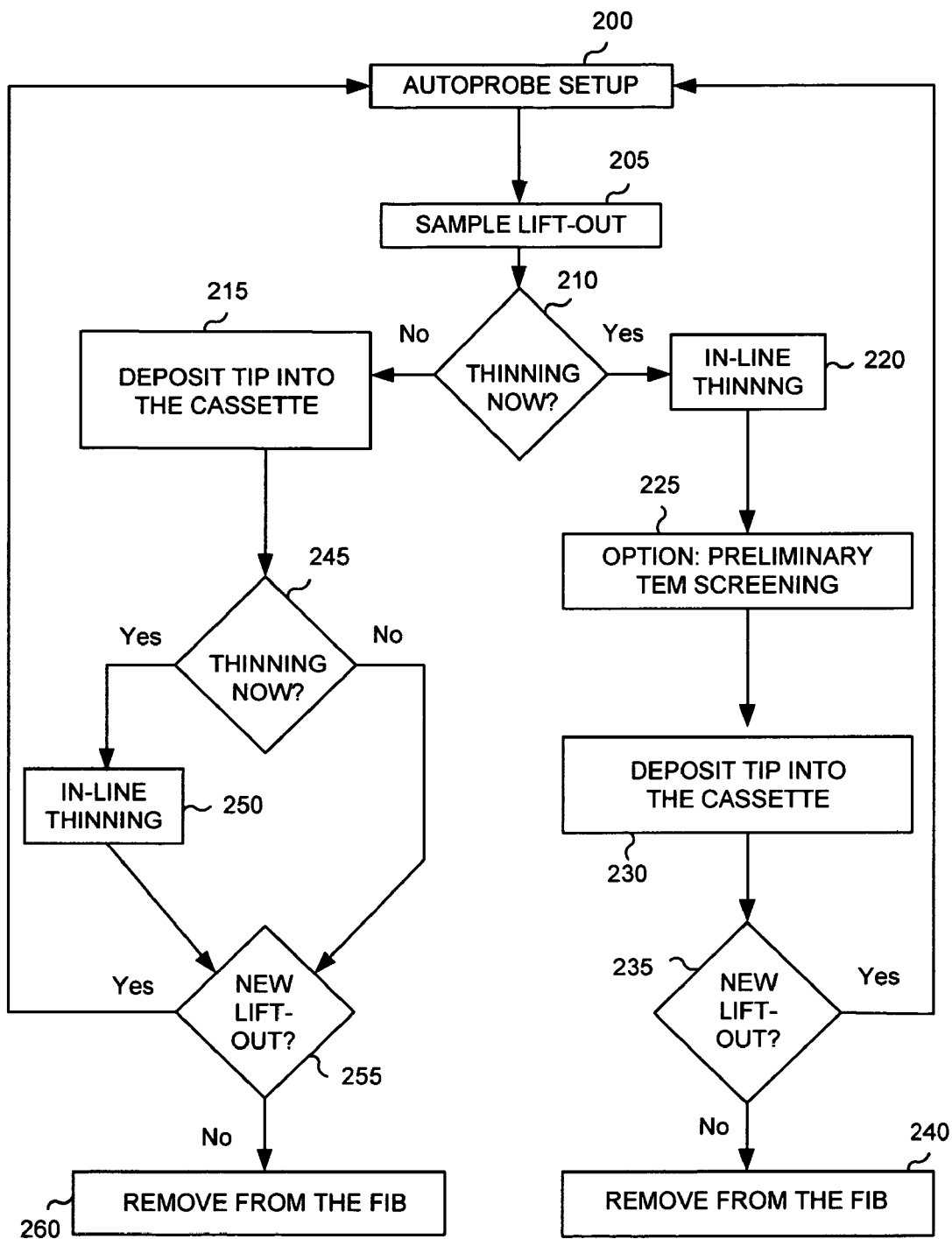
FIG. 2 is a flow diagram of the automated sample lift-out and delivery method of the preferred embodiment

The sample lift-out step (205), described in FIG. 2, includes the means for locating the probe tip (140) by, for example, the parallax method, as is known in the art; contact detection realized by means of strain or optical methods, for example, and the location of an area of interest, using a predetermined list of target locations and image recognition of surface features or added landmarks for registration. The optical method comprises a light detector for measuring the changed intensity of light reflected from a probe tip (140) or a capsule (not shown) attached to the probe tip (140), the probe tip (140) is displaced by surface contact. Novel contact-detection methods are described in co-pending application Ser. No. 11/186,072, described above, and in another co-pending application relating to optical apparatus and methods to be filed, also claiming priority from the provisional application referenced above.

Figure 3:
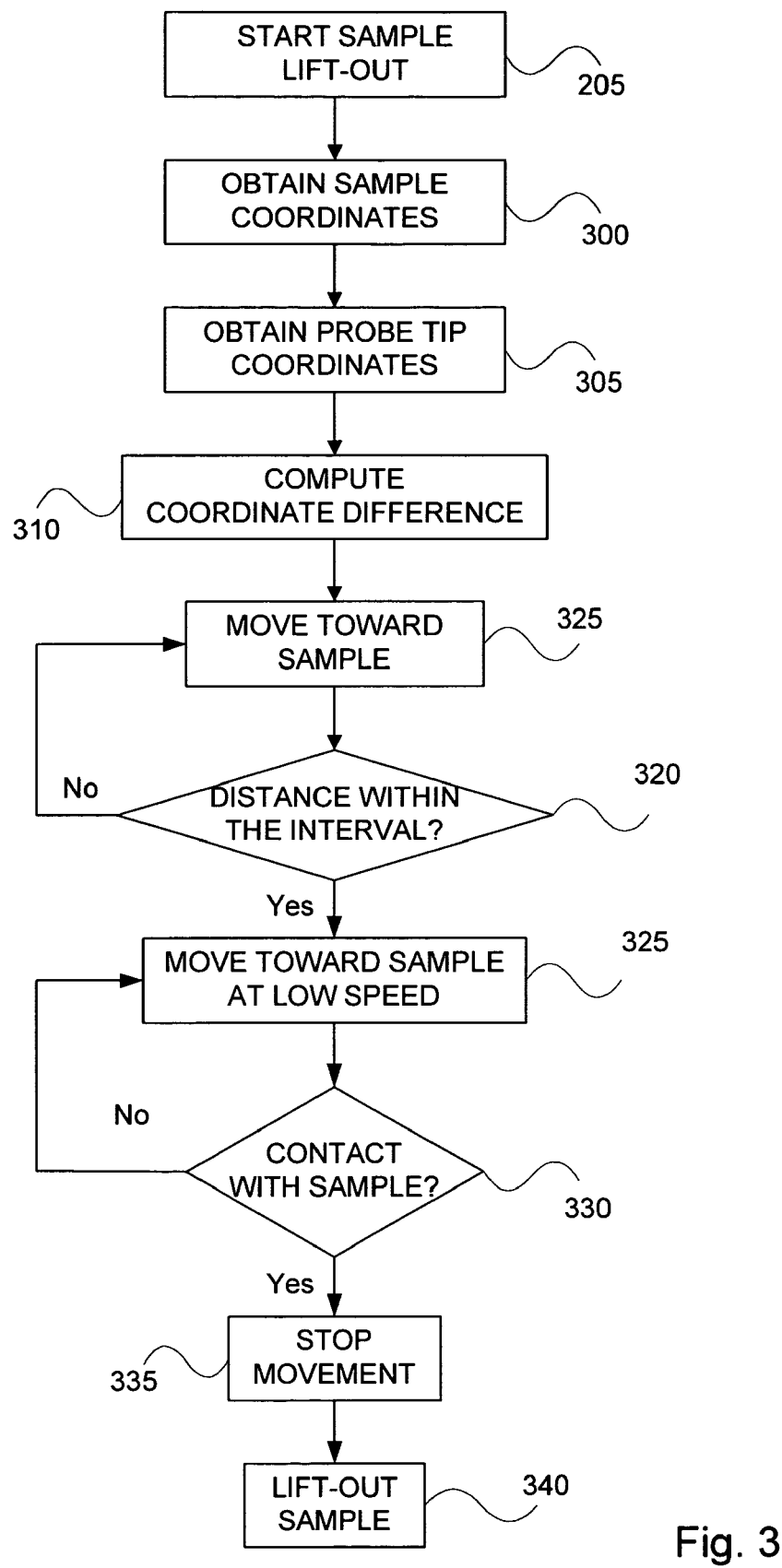
FIG. 3 is a flow diagram of the sample-lift out process of the preferred embodiment.

As shown in FIG. 3, the sample lift-out process starts when the automated program obtains co-ordinates for the specimen (125) at step (300) and for the probe tip (140) at step (305), according to means just discussed. At step (310), the program computes the coordinate difference and the required motion commands to the motion controllers (110). Step (320) checks to determine if the probe tip (140) is close to the specimen (125) within some pre-determined distance of the desired sample location. When the pre-determined distance is reached, motion continues at a lower speed in step (325) until contact with the sample (150) is detected at step (330) and motion stops at step (335). At step (340) the sample (150) is excised from the specimen (125), attached to a probe tip (140) and lifted out of the specimen (125). After the sample (150) is excised from a specimen (125), a probe tip (140) can be connected to it using, for instance, one of the methods disclosed in U.S. Pat. No. 6,570,170, referred to above.

Returning to FIG. 2, the automated process continues after sample lift-out. The sample is either attached to a TEM sample holder (not shown) for subsequent thinning, or it is immediately thinned and then later attached to the TEM sample holder, all as part of the sample lift-out step (205).

The location of the sample (150) or probe tip (140) in the specimen chamber can be determined by the parallax method. This method allows bringing the probe tip (140) to the target position on the specimen (125) surface or cassette (160) using incremental movements followed by comparison of consecutive scanned images from at least two perspectives. This comparison of images can be part of an automated process using image recognition.

An area of interest on a specimen (125) can be located as follows: The specimen (125) is delivered into a FIB vacuum chamber and placed into a specified location. Special markings previously made around the area of interest, typically by laser or ion beam milling or deposition can be easily detected by the automated system using image recognition. Alternatively, image recognition can be used to locate specific features on the surface of the specimen (125) for navigation to the test point, or CAD (Computer Automated Design) navigation can be used to translate the specimen stage (120) to the target point based on registration marks on the surface of the specimen (125), all as is known in the art.

The sample lift-out step (205) can be done by different methods, such as that described in U.S. Pat. No. 6,570,170, referred to above. This procedure can be carried through the step of attachment of the lift-out sample (150) to a TEM sample holder (not shown), or the procedure can be interrupted after the lift-out sample (150) has been attached to the probe tip (140) and lifted out of the specimen (125). The exact extent of completion of the lift-out procedure will depend on the optional method selected for creating the TEM sample; that is combining the lift-out sample (150) with the TEM sample holder. Successful lift-out can be verified as part of the automated process using image recognition.

After the sample lift-out process (205) is completed, there are two optional flows for the automated sample lift-out process: one for immediate sample thinning "in-line thinning" (220), using the focused ion beam milling process available at the same in-line FIB, or another flow for thinning later during the course of operation. Alternatively, the thinning can be performed either inside the in-line FIB later on as part of the automated sample lift-out process, or in the off-line FIB after the automated sample lift-out process is finished.

If in-line thinning is selected at step (210) to be done later, the tip (140) with sample (150) attached is deposited into a cassette (160) at step 215. If a choice is made at step (245) to commence thinning, this is done at step (250). Either way, the process flows to the decision at step 255 to determine if another sample (150) is to be removed. If so, execution returns to step (200); else, at step 260, the tip (140) and attached sample (150) are removed from the FIB. After removal from the FIB, the tip (140) and attached sample (150) can be joined to a TEM grid or holder as described in one or more of the co-pending applications.

If, at step 210, in-line thinning of the sample (150) is selected, such thinning is done at step (220). The sample (150) so thinned may be be optionally subjected to TEM screening at step (225), and then deposited into the cassette (160) at step (230). Decision step (235) decides if a new sample is to be lifted out; if so, execution returns to step (200), if not, the tip (140) and sample (150) can be removed from the FIB at step 240, and further processed as just discussed.

Since those skilled in the art can modify the specific embodiments described above, we intend that the claims be interpreted to cover such modifications and equivalents.

We claim:

1. An apparatus for performing automated in-situ lift-out of a sample from a specimen, the apparatus comprising:
   a computer; the computer further comprising:
      a memory;
      the memory holding computer-readable instructions;

a stage for a specimen;
  the stage connected to one or more stage motion controllers
  the stage motion controllers connected to the computer;
a nano-manipulator;
  the nano-manipulator connected to one or more nano-manipulator motion controllers;
  the nano-manipulator motion controllers connected to the computer;
the nano-manipulator having a probe tip;
a means for detecting when the probe tip makes contact with a surface;
  the means for detecting when the probe tip makes contact with a surface connected to the computer; and,
the computer-readable instructions comprising instructions to cause the stage motion controllers and the nano-manipulator motion controllers to automatically perform in-situ lift-out of a sample from the specimen.

2. The apparatus of claim 1 further comprising:
a ion-beam source; the ion-beam source operatively connected to the computer.

3. The apparatus of claim 1 further comprising:
an electron-beam source; the electron-beam source operatively connected to the computer.

4. The apparatus of claim 1 where the means for detecting when the probe tip makes contact with a surface comprises a strain gauge.

5. The apparatus of claim 1 where the means for detecting when the probe makes contact with a surface comprises a light detector for measuring the change of intensity of reflected light as the probe tip is displaced by surface contact.

6. The apparatus of claim 1, further comprising a focused ion beam instrument; the stage for a specimen disposed inside the focused ion beam instrument.

7. An apparatus for performing automated in-sit lift-out of a sample from a specimen, the apparatus comprising:
  a computer; the computer further comprising:
    a memory;
    the memory holding computer-readable instructions;
  a stage for a specimen;
    the stage connected to one or more stage motion controllers
    the stage motion controllers connected to the computer;
  a nano-manipulator;
    the nano-manipulator connected to one or more nano-manipulator motion controllers;
    the nano-manipulator motion controllers connected to the computer; and,
  the computer-readable instructions comprising instructions to cause the stage motion controllers and the nano-manipulator motion controllers to automatically perform in-situ lift-out of a sample from the specimen.

8. The apparatus of claim 7 further comprising:
an ion-beam source; the ion-beam source operatively connected to the computer.

9. The apparatus of claim 7 further comprising:
an electron-beam source; the electron-beam source operatively connected to the computer.

10. The apparatus of claim 7, further comprising a focused ion beam instrument; the stage for a specimen disposed inside the focused ion beam instrument.

11. An apparatus for performing automated in-situ lift-out of a sample from a specimen, the apparatus comprising:
  a focused ion beam instrument;
  a computer; the computer further comprising:
    a memory;
    the memory holding computer-readable instruction;
  a stage for a specimen;
    the stage for a specimen disposed within the focused ion beam instrument;
    the stage connected to one or more stage motion controllers
    the stage motion controllers connected to the computer;
  an electron-beam source;
    the electron-beam source operatively connected to the computer;
  an ion-beam source;
    the ion-beam source operatively connected to the computer;
  a nano-manipulator;
    the nano-manipulator connected to one or more nano-manipulator controllers;
    the nano-manipulator motion controllers connected to the computer;
  the nano-manipulator having a probe tip;
  a strain gauge for detecting when the probe tip makes contact with a surface;
    the strain gauge connected to the computer; and,
  the computer-readable instructions comprising instructions to cause the stage motion controllers, the nano-manipulator motion controllers, and the ion-beam source to automatically perform in-situ lift-out of a sample from the specimen.

12. A method for preparing a sample from a specimen for analysis, in an apparatus comprising: a nano-manipulator probe; the nano-manipulator probe having a probe tip, a cassette for receiving probe tips, and an ion-beam source; the method comprising:
  performing lift-out of the sample from the specimen;
    where the sample is attached to the probe tip;
  thinning the sample with the ion beam for TEM Inspection; and,
  depositing the probe tip and sample in the cassette.

13. The method of claim 12 where the step of performing lift-out of the sample further comprises:
  obtaining coordinates of the sample area on the specimen;
  obtaining coordinates of the probe tip;
  computing the difference in coordinates of the sample and the probe tip;
  moving the probe tip toward the sample until the difference in coordinates of the sample and the probe tip is less than a predetermined distance;
  moving the probe tip toward the sample at a reduced speed until contact with the sample;
  excising the sample from the specimen;
  attaching the sample to the probe tip.

14. The method of claim 13 where the step of moving the probe tip toward the sample at a reduced speed until contact with the sample is made further comprises:
  detecting contact with the sample by measuring the output of a strain gauge.

15. The method of claim 13 where the step of moving the probe tip toward the sample at a reduced speed until contact with the sample is made further comprises:
  detecting contact with the sample by measuring the output of a light detector.

16. The method of claim 12 further comprising:
  providing a focused ion-beam instrument; and,
  performing the lift-out of the sample from the specimen inside the chamber of the focused ion-beam instrument.

17. The method of claim 16 further comprising:
  selectively performing another sample lift-out and thinning before removing the cassette from the chamber of the focused ion-beam instrument.

18. A method for preparing a sample from a specimen for analysis, in an apparatus comprising: a nano-manipulator probe; the nano-manipulator probe having a probe tip, a cassette for receiving probe tips, and an ion-beam source; the method comprising:
performing lift-out of the sample from the specimen;
where the sample is attached to the probe tip;
depositing the probe tip and sample in the cassette; and,
thinning the sample with the ion beam for TEM inspection.

19. The method of claim 18 where the step of performing lift-out of the sample further comprises:
obtaining coordinates of the sample area on the specimen;
obtaining coordinates of the probe tip;
computing the difference in coordinates of the sample and the probe tip;
moving the probe tip toward to sample until the difference in coordinates of the sample and the probe tip is less than a predetermined distance;
moving the probe tip toward the sample at a reduced speed until contact with the sample;
excising the sample from the specimen;
attaching the sample to the probe tip.

20. The method of claim 18 where the step of moving the probe tip toward the sample at a reduced speed until contact with the sample is made further comprises:
detecting contact with the sample by measuring the output of a strain gauge.

21. The method of claim 18 where the step of moving the probe tip toward the sample at a reduced speed until contact with the sample is made further comprises:
detecting contact with the sample by measuring the output of a light detector.

22. The method of claim 18 further comprising:
providing a focused ion-beam instrument; and,
performing the lift-out of the sample from the specimen inside the chamber of the focused ion-beam instrument.

23. The method of claim 22 further comprising:
selectively performing another sample lift-out and thinning before removing the cassette from the chamber of the focused ion-beam instrument.

24. A computer-readable medium having computer-executable instructions for performing a method for implementing automated in-situ lift-out and analysis of a sample from a specimen in an apparatus comprising: a nano-manipulator probe; the nano-manipulator probe having a probe tip, a cassette for receiving probe tips, and an ion-beam source; the method comprising:
performing lift-out of the sample from the specimen;
where the sample is attached to the probe tip;
thinning the sample with the ion beam for TEM inspection; and,
depositing the probe tip and sample in the cassette.

25. The computer-readable medium of claim 24 where the method for implementing automated in-situ lift-out and analysis further comprises:
obtaining coordinates of the sample on the specimen;
obtaining coordinates of the probe tip;
computing the difference in coordinates of the sample and the probe tip;
moving probe tip toward the sample until the difference in coordinates of the sample and the probe tip is less than a predetermined distance;
moving the probe tip toward the sample at a reduced speed until contact with the sample;
excising the sample from the specimen;
attaching the sample to the probe tip.

26. The computer-readable medium of claim 24 where the method for implementing automated in-situ lift-out and analysis further comprises: further comprises:
detecting contact with the sample by measuring the output of a strain gauge.

27. The computer-readable medium of claim 24 where the method for implementing automated in-situ lift-out and analysis further comprises:
detecting contact with the sample by measuring the output of a light detector.

28. The computer-readable medium of claim 24 where the method for implementing automated in-situ lift-out and analysis further comprises:
providing a focused ion-beam instrument; and,
performing the lift-out of the sample from the specimen inside the chamber of the focused ion-beam instrument.

29. The computer-readable medium of claim 24 where the method for implementing automated in-situ lift-out and analysis further comprises:
selectively performing another sample lift-out and thinning before removing the cassette from the chamber of the focused ion-beam instrument.

30. A computer-readable medium having computer-executable instructions for performing a method for implementing automated in-situ lift-out and analysis of a sample from a specimen for analysis, in an apparatus comprising: a nano-manipulator probe; the nano-manipulator probe having a probe tip, a cassette for receiving probe tips, and an ion-beam source; the method comprising:
performing lift-out of the sample from the specimen;
where the sample is attached to the probe tip;
depositing the probe tip and sample in the cassette; and,
thinning the sample with the ion beam for TEM inspection.

31. The computer-readable medium of claim 30 where the method for implementing automated in-situ lift-out and analysis further comprises:
obtaining coordinates of the sample on the specimen;
obtaining coordinates of the probe tip;
computing the difference in coordinates of the sample and the probe tip;
moving the probe tip toward the sample until the difference in coordinates of the sample and the probe tip is less than a predetermined distance;
moving the probe tip toward the sample at a reduced speed until contact with the sample;
excising the sample from the specimen;
attaching the sample to the probe tip.

32. The computer-readable medium of claim 30 where the method for implementing automated in-situ lift-out and analysis further comprises:
detecting contact with the sample by measuring the output of a strain gauge.

33. The computer-readable medium, of claim 30 where the method for implementing automated in-situ lift-out and analysis further comprises:
detecting contact with the sample by measuring the output of a light detector.

34. The computer-readable medium of claim 30 where the method for implementing automated in-situ lift-out and analysis further comprises:
providing a focused ion-beam instrument; and,
performing the lift-out of the sample from the specimen inside the chamber of the focused ion-beam instrument.

35. The computer-readable medium of claim 34 where the method for implementing automated in-situ lift-out and analysis further comprises:

selectively performing another sample lift-out and thinning before removing the cassette from the chamber of the focused ion-beam instrument.

36. The apparatus of claim 1, where the means far detecting when the probe makes contact with a surface further comprises:
the computer-readable instructions further comprising an image-recognition process for detecting when the probe makes contact with a surface.

37. An apparatus for performing automated in-situ lift-out of a sample from a specimen, the apparatus comprising:
a focused ion beam instrument;
a computer; the computer further comprising:
a memory;
the memory holding computer-readable instructions;
a stage for a specimen;
the stage for a specimen disposed within the focused ion beam instrument;
the stage connected to one or more stage motion controllers
the stage motion controllers connected to the computer;
an electron-beam source;
the electron-beam source operatively connected to the computer;
an ion-beam, source;
the ion-beam source operatively connected to the computer;
a nano-manipulator;
the nano-manipulator connected to one or more nano-manipulator controllers;
the nano-manipulator motion controllers connected to the computer;
the nano-manipulator having a probe tip;
an image-recognition system for detecting when the probe tip makes contact with a surface; and,
the computer-readable instructions comprising instructions to cause the stage motion controllers, the nano-manipulator motion controllers, and the ion-beam source to automatically perform in-situ lift-out of a sample from the specimen.

38. The method of claim 13 where the step of moving the probe tip toward the sample at a reduced speed until contact with the sample is made further comprises:
moving the probe tip toward the sample until the difference in coordinates of the sample and the probe tip is zero.

39. The method of claim 19 where the step of moving the probe tip toward the sample at a reduced speed until contact with the sample is made further comprises:
moving the probe tip toward the sample until the difference in coordinates of the sample and the probe tip is zero.

40. The computer-readable medium of claim 25 where the method for implementing automated in-sit lift-out and analysis further comprises:
moving the probe tip toward the sample until the difference in coordinates of the sample and the probe tip is zero.

41. The computer-readable medium of claim 31 where the method for implementing automated in-situ lift-out and analysis further comprises:
moving the probe tip toward the sample until the difference in coordinates of the sample and the probe tip is zero.

42. A method for preparing a sample from a specimen for analysis, in an apparatus comprising: a nano-manipulator probe; the nano-manipulator probe having a probe tip, a cassette for receiving probe tips, and an ion-beam source; the method comprising:
performing lift-out of the sample from the specimen;
where the step of performing lift-out of the sample further comprises:
excising the sample from the specimen;
obtaining coordinates of the sample area on the specimen;
obtaining coordinates of the probe tip;
computing the difference in coordinates of the sample and the probe tip;
moving the probe tip toward the sample until the difference in coordinates of the sample and the probe tip is less than a predetermined distance;
moving the probe tip toward the sample at a reduced speed until contact with the sample;
attaching the sample to the probe tip;
thinning the sample with the ion beam for TEM inspection; and,
depositing the probe tip and sample in the cassette.

43. The method of claim 42 where the step of moving the probe tip toward the sample at a reduced speed until contact with the sample is made further comprises:
detecting contact with the sample by measuring the output of a strain gauge.

44. The method of claim 42 where the step of moving the probe tip toward the sample at a reduced speed until contact with the sample is made further comprises:
detecting contact with the sample by measuring the output of a light detector.

45. The method of claim 42 where the step of moving the probe tip toward the sample at a reduced speed until contact with the sample is made further comprises:
moving the probe tip toward the sample until the difference in coordinates of the sample and the probe tip is zero.

46. The method of claim 42 further comprising:
providing a focused ion-beam instrument; and,
performing the lift-out of the sample from the specimen inside the chamber of the focused ion-beam instrument.

47. The method of claim 46 further comprising:
selectively performing another sample lift-out and thinning before removing the cassette from the chamber of the focused ion-beam instrument.

48. A method for preparing a sample from a specimen for analysis, in an apparatus comprising: a nano-manipulator probe; the nano-manipulator probe having a probe tip, a cassette for receiving probe tips, and an ion-beam source; the method comprising:
performing lift-out of the sample from the specimen;
where the performing of lift-out of the sample further comprises:
excising the sample from the specimen;
obtaining coordinates of the sample area on the specimen;
obtaining coordinates of the probe tip;
computing the difference in coordinates of the sample and the probe tip;
moving the probe tip toward the sample until the difference in coordinates of the sample and the probe tip is less than a predetermined distance;
moving the probe tip toward the sample at a reduced speed until contact withh the sample;
attaching the sample to the probe tip;
depositing the probe tip and sample in the cassette; and,
thinning the sample withh the ion beam for TEM inspection.

49. The method of claim 48 where the step of moving the probe tip toward the sample at a reduced speed until contact withh the sample is made further comprises:

50. The method of claim 48 where the step of moving the probe tip toward the sample at a reduced speed until contact withh the sample is made further comprises:
  detecting contact withh the sample by measuring the output of a light detector.

51. The method of claim 48 where the step of moving the probe tip toward the sample at a reduced speed until contact withh the sample is made further comprises:
  moving the probe tip toward the sample until the difference in coordinates of the sample and the probe tip is zero.

52. The method of claim 48 further comprising:
  providing a focused ion-beam instrument; and,
  performing the lift-out of the sample from the specimen inside the chamber of the focused ion-beam instrument.

53. The method of claim 52 further comprising:
  selectively performing another sample lift-out and thinning before removing the cassette from the chamber of the focused ion-beam instrument.

54. A computer-readable medium having computer-executable instructions for performing a method for implementing automated in-situ lift-out and analysis of a sample from a specimen in an apparatus comprising: a nano-manipulator probe; the nano-manipulator probe having a probe tip, a cassette for receiving probe tips, and an ion-beam source; the method comprising:
  performing lift-out of the sample from the specimen;
  where the performing of lift-out of the sample further comprises:
    excising the sample from the specimen;
    obtaining coordinates of the sample on the specimen;
    obtaining coordinates of the probe tip;
    computing the difference in coordinates of the sample and the probe tip;
    moving the probe tip toward the sample until the difference in coordinates of the sample and the probe tip is less then a predetermined distance;
    moving the probe tip toward the sample at a reduced speed until contact withh the sample;
    attaching the sample to the probe tip;
  thinning the sample withh the ion beam for TEM inspection; and,
  depositing the probe tip and sample in the cassette.

55. The computer-readable medium of claim 54 where the method for implementing automated in-situ lift-out and analysis further comprises:
  detecting contact with the sample by measuring the output of a strain gauge.

56. The computer-readable medium of claim 54 where the method for implementing automated in-situ lift-out and analysis further comprises:
  detecting contact withh the sample by measuring the output of a light detector.

57. The computer-readable medium of claim 54 where the method for implementing automated in-situ lift-out and analysis further comprises:
  moving the probe tip toward the sample until the difference in coordinates of the sample and the probe tip is zero.

58. The computer-readable medium of claim 54 where the method for implementing automated in-situ lift-out and analysis further comprises:
  providing a focused ion-beam instrument; and,
  performing the lift-out of the sample from the specimen inside the chamber of the focused ion-beam instrument.

59. The computer-readable medium of claim 58 where the method for implementing automated in-situ lift-out and analysis further comprises:
  selectively performing another sample lift-out and thinning before removing the cassette from the chamber of the focused ion-beam instrument.

60. A computer-readable medium having computer-executable instructions for performing a method for implementing automated in-situ lift-out and analysis of a sample from a specimen in an apparatus comprising: a nano-manipulator probe; the nano-manipulator probe having a probe tip, a cassette for receiving probe tips, and an ion-beam source; the method comprising:
  performing lift-out of the sample from the specimen;
  where the performing of lift-out of the sample further comprises:
    excising the sample from the specimen;
    obtaining coordinates of the sample on the specimen;
    obtaining coordinates of the probe tip;
    computing the difference in coordinates of the sample and the probe tip;
    moving the probe tip toward the sample until the difference in coordinates of the sample and the probe tip is less than a predetermined distance;
    moving the probe tip toward the sample at a reduced speed until contact withh the sample;
    attaching the sample to the probe tip;
  depositing the probe tip and sample in the cassette; and,
  thinning the sample withh the ion beam for TEM inspection.

61. The computer-readable medium of claim 54 where the method for implementing automated in-situ lift-out and analysis further comprises:
  detecting contact withh the sample by measuring the output of a strain gauge.

62. The computer-readable medium of claim 54 where the method for implementing automated in-situ lift-out and analysis further comprises:
  detecting contact withh the sample by measuring the output of a light detector.

63. The computer-readable medium of claim 54 where the method for implementing automated in-situ lift-out and analysis further comprises:
  moving the probe tip toward the sample until the difference in coordinates of the sample and the probe tip is zero.

64. The computer-readable medium of claim 60 where the method for implementing automated in-situ lift-out and analysis further comprises:
  providing a focused ion-beam instrument; and,
  performing the lift-out of the sample from the specimen inside the chamber of the focused ion-beam instrument.

65. The computer-readable medium of claim 64 where the method for implementing automated in-situ lift-out and analysis further comprises:
  selectively performing another sample lift-out and thinning before removing the cassette from the chamber of the focused ion-beam instrument.

* * * * *

UNITED STATES PATENT AND TRADEMARK OFFICE
CERTIFICATE OF CORRECTION

PATENT NO. : 7,414,252 B2  Page 1 of 1
APPLICATION NO. : 11/265934
DATED : August 19, 2008
INVENTOR(S) : Thomas M. Moore and Lyudmila Zaykova-Feldman It is certified that error appears in the above-identified patent and that said Letters Patent is hereby corrected as shown below:

In the claims:

Column 7, line 16, the word "to" should be --the--.
Column 7, line 61, the word --the-- should be inserted between moving and probe.
Column 9, line 4, the word "far" should be --for--.
Column 9, line 6, the "," between beam and source should be removed.
Column 10, line 60, and line 67, Column 11, lines 1, 5, 10, 40, 42, and 52, the word "withh" should be --with--.
Column 10, line 63, the word "withh" should be --with--.
Column 12, lines 29, 32, 37, and 42, the word "withh" should be --with--.

Signed and Sealed this

Twenty-first Day of October, 2008

JON W. DUDAS
*Director of the United States Patent and Trademark Office*